US010010685B2

(12) United States Patent
Ferreri et al.

(10) Patent No.: US 10,010,685 B2
(45) Date of Patent: Jul. 3, 2018

(54) SINGLE USE DELIVERY DEVICE HAVING A PRIMER ELEMENT

(71) Applicant: Becton, Dickinson and Company, Franklin Lakes, NJ (US)

(72) Inventors: Suzanne Ferreri, Ridgewood, NJ (US); Darrin Manke, North Andover, MA (US); James J. Kennedy, III, Mont Vernon, NH (US); Morgan Carlson, Lowell, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 179 days.

(21) Appl. No.: 13/925,213

(22) Filed: Jun. 24, 2013

(65) Prior Publication Data

US 2013/0345673 A1 Dec. 26, 2013

Related U.S. Application Data

(60) Provisional application No. 61/664,456, filed on Jun. 26, 2012.

(51) Int. Cl.
*A61M 5/36* (2006.01)
*A61M 25/00* (2006.01)
(Continued)

(52) U.S. Cl.
CPC ............... *A61M 5/36* (2013.01); *A61J 1/067* (2013.01); *A61J 1/2093* (2013.01); *A61M 5/282* (2013.01);
(Continued)

(58) Field of Classification Search
CPC ...... A61M 5/3146; A61M 5/36; A61M 5/282; Y10S 215/90; Y10S 215/03
See application file for complete search history.

(56) References Cited

U.S. PATENT DOCUMENTS 3,340,869 A * 9/1967 Bane ................. A61M 3/00
206/364
4,131,217 A * 12/1978 Sandegren ......... B65D 83/0094
222/103

(Continued)

FOREIGN PATENT DOCUMENTS

EP 0352348 1/1990
EP 0702968 3/1996
WO 95/27522 A1 10/1995

OTHER PUBLICATIONS

PCT International Search Report and Written Opinion in PCT/US2013/047874, dated Jan. 29, 2014, 17 pages.

*Primary Examiner* — Laura Bouchelle
(74) *Attorney, Agent, or Firm* — Servilla Whitney LLC

(57) ABSTRACT

A single use delivery device is disclosed having a manually deformable liquid container defining an inner chamber, the container having a distal end, a body, a proximal end, and an outlet on the distal end; a tip projecting from the outlet on the distal end of the container, the tip in fluid communication with the inner chamber of the container; and a primer element for removing one or more air bubbles from the chamber, said primer element being attached to and in fluid communication with the deformable container. A method of administering a fluid to or flushing a vascular access device using a single use pre-filled delivery device as described herein is also disclosed.

7 Claims, 22 Drawing Sheets

(51) Int. Cl.
    *A61J 1/06*     (2006.01)
    *A61M 5/28*     (2006.01)
    *A61M 39/24*    (2006.01)
    *A61J 1/20*     (2006.01)
    A61M 5/31       (2006.01)
    A61J 1/14       (2006.01)

(52) U.S. Cl.
    CPC ............ *A61M 5/284* (2013.01); *A61M 25/00* (2013.01); *A61M 39/24* (2013.01); *A61J 1/1425* (2015.05); *A61M 2005/312* (2013.01); *A61M 2005/3123* (2013.01); *A61M 2025/0019* (2013.01)

(56) References Cited

U.S. PATENT DOCUMENTS

| | | |
|---|---|---|
| 5,333,761 A | 8/1994 | Davis et al. |
| 5,683,369 A | 11/1997 | Tsukada |
| 6,383,166 B1 * | 5/2002 | Farris .................... A61M 5/282 222/94 |
| 2005/0203463 A1 | 9/2005 | Lampropoulos |
| 2006/0131189 A1 | 6/2006 | Lee et al. |
| 2007/0262091 A1 | 11/2007 | Harper |

* cited by examiner

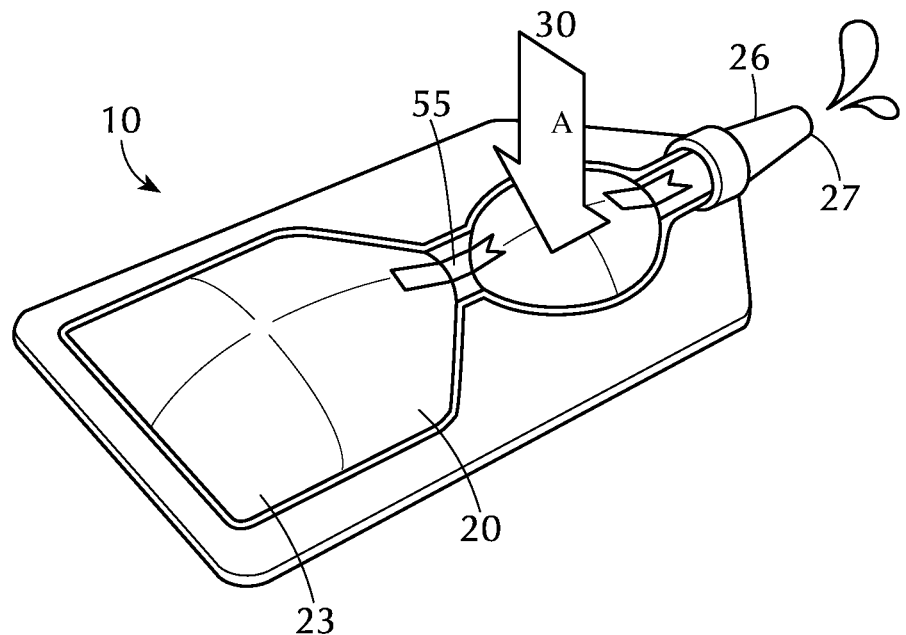
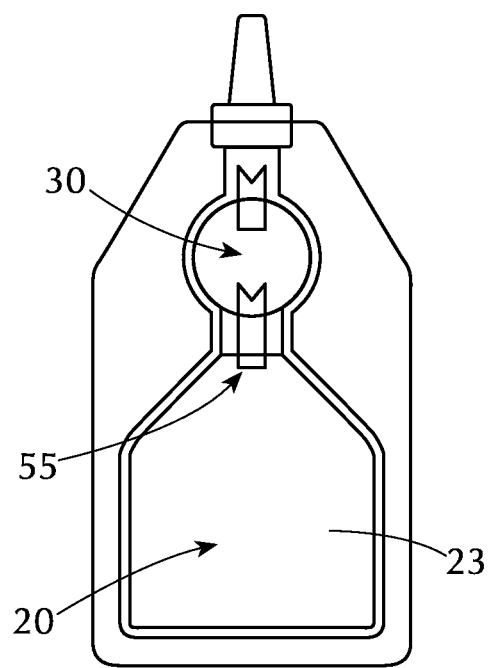
FIG. 26

SINGLE USE DELIVERY DEVICE HAVING A PRIMER ELEMENT

CROSS-REFERENCE TO RELATED APPLICATIONS

This application claims priority under 35 U.S.C. § 119(e) to U.S. Provisional Application No. 61/664,456, filed Jun. 26, 2012, the disclosures of which are incorporated herein by reference in their entirety.

TECHNICAL FIELD

An aspect of the invention relates generally to a single use pre-filled delivery device having a manually deformable liquid container defining an inner chamber, a tip projecting from the outlet on the distal end of the container, and a primer element for removing one or more air bubbles from the chamber. The container includes a distal end, a body, a proximal end, and an outlet on the distal end. The tip is in fluid communication with the inner chamber of the container. The primer element is attached to and in fluid communication with the deformable container. Another aspect of the invention relates generally to a method of administering a fluid to or flushing a vascular access device using the single use pre-filled delivery device described herein.

BACKGROUND

Vascular access devices (VAD) used to access a patient's vascular space without puncture using a hypodermic needle. Vascular Access Devices (VADs) include intravenous catheters, syringes, extension sets, stop cocks, tubing, high pressure extension tubing, and needleless access devices. These devices are used in patients where frequent access is required to the vascular space for delivery of treatment and withdraw of fluids. Indwelling vascular access devices are susceptible to infection and occlusion, requiring continued preventive maintenance. To ensure VADs are used properly and do not become occluded, standards of practice have been developed to maintain the indwelling VAD. These standards include a cleaning procedure, which is commonly referred to as a flush procedure. One form of VAD maintenance is a continuous saline dip where which a saline bag is connected to the VAD and provides continuous flow of saline solution to the patient through the VAD. This approach may put the patient at risk by delivering excess fluid to the vascular space.

An alternative method for vascular device maintenance, known as flushing, involves intermittent delivery of saline thru the VAD using a hypodermic syringe. One way to deliver intermittent saline to the VAD is to fill a hypodermic syringe fitted with a needle from a saline vial or ampoule. The filled syringe is then connected to the VAD and the saline is then flushed thru the VAD into the patient. Pre-filled delivery containers may be used to deliver sterile contents to a receiving connection. Use of pre-filled saline flush syringes to deliver saline flush to VAD's offers improved safety and efficiency over manually filled hypodermic syringes.

The containers may be formed using a variety of manufacturing processes including but not limited to extrusion molding, injection molding and blow fill seal molding. When a device is closed or sealed, however, a portion of the contained volume may be comprised of air. During use, it may be necessary to remove the air within through a step known as priming. The end result is a primed device where the internal surfaces of the device make contact with only the pre-filled solution and not air.

It is also important in the flush procedure not to draw blood back into the catheter where it can clot and seal the catheter, commonly referred to as "reflux". In order to prevent blood reflux into the catheter the user is encouraged to maintain a positive pressure in the line during the flush procedure. This may involve clamping the IV line and withdrawing the syringe and cannula from the IV port while still applying pressure to the syringe plunger rod during the flush procedure. When using a conventional syringe with an elastomeric stopper, the stopper is often compressed when it contacts the distal end of the syringe barrel at the completion of the flush procedure. When a user relieves the pressure to the plunger after the flush procedure is completed, the stopper will expand back to its normal size thereby withdrawing liquid from the catheter into the syringe barrel. This is undesirable, since it can cause blood to enter the catheter at the catheter distal end (reflux) where it will remain stationary until the next time the VAD is used.

Although a wide variety of catheters and I.V. ports can be adequately flushed using currently available syringe assemblies, as flushing practices change from continuous IV drip to intermittent flushing, there is a need for a new sterile, single use, pre-filled delivery device for maintenance of VAD's that reduces reflux while removing unwanted air from the delivery chamber of a closed pre-filled container.

SUMMARY

An embodiment of the present invention is directed to a single use delivery device having a manually deformable liquid container defining an inner chamber, a tip projecting from the outlet on the distal end of the container, and a primer element for removing one or more air bubbles from the chamber. The container includes a distal end, a body, a proximal end, and an outlet on the distal end. The tip is in fluid communication with the inner chamber of the container and is releasably engageable to a vascular access device. The vascular access device may be a syringe, extension set, intravenous set, stop cock, tubing, high pressure extension tubing, or needleless connector.

The primer element is attached to and in fluid communication with the deformable container. The primer element may be assembled into the body of the container or it may be molded into the body of the container. The primer element may be positioned on the proximal end of the container.

In one or more embodiments, the primer element may be in the form of a collapsible button which is convex prior to the primer being manually depressed and is concave after the primer is manually depressed.

In one or more embodiments, the primer element includes a thumb press located at the proximal end of the container and the body of the container comprises a plurality of collapsible funnel-shaped, concentrically-arranged side walls, wherein the diameters of the concentrically-arranged walls decrease from the distal end to the proximal end of the liquid container.

In an alternate embodiment, the primer element includes a thumb press located at the proximal end of the container and the body of the container comprises a plurality of collapsible funnel-shaped, nonconcentrically-arranged side walls, wherein the diameters of the nonconcentrically-arranged walls decrease from the distal end to the proximal end of the liquid container.

In yet another embodiment, the primer element may be in the form of a series of two or more adjoining collapsible buttons in fluid communication.

In one or more embodiments, the single use delivery device includes a pre-selected amount of fluid in the chamber.

The deformable container may be made of thermoplastic elastomers.

Another embodiments of the present invention is directed to a method of delivery fluid to a vascular access device comprising providing a single use delivery device having a manually deformable liquid container defining an inner chamber, the container having a distal end, a body, a proximal end, and an outlet on the distal end; a tip projecting from the outlet on the distal end of the container, the tip in fluid communication with the inner chamber of the container; and a primer element for removing one or more air bubbles from the chamber, said primer element being attached to and in fluid communication with the deformable container; providing a vascular access device having a proximal end, a distal end, and a passageway therethrough, the proximal end having a female luer tip in fluid communication with the passageway; placing the distal end of the vascular access device in a blood vessel of a patient; depressing the primer element to evacuate air within the chamber; engaging the male tip of the container with the female tip of the vascular access device; applying force to deform the container so that a solution located in the chamber flows through the one-way valve into the vascular access device; and disengaging the male tip of the container from the female tip of the vascular access device.

An embodiments of the present invention is directed to a single use delivery device including a manually deformable liquid container defining an inner chamber, the container having a distal end, a proximal end, and an outlet on the distal end; a tip projecting from the outlet on the distal end of the container, the tip in fluid communication with the inner chamber of the container; a primer element for collapsing a portion of the deformable container for driving air out of said chamber by depressing the primer element, said primer element being attached to the deformable container; and a one-way valve disposed between the tip and the deformable container, the one-way valve in fluid communication with the inner chamber of the container, said one-way valve permitting air or fluid evacuation from the inner chamber but preventing air or fluid intake into the inner chamber when the container is manually deformed and released.

The one-way valve prevents reflux of solution in the passageway. The one-way valve may be a duckbill valve, an umbrella valve, a ball-check valve, diaphragm check valve, swing check valve, stop-check valve, lift-check valve or a combination thereof.

Another aspect of the present invention pertains to a method of delivery fluid to a vascular access device comprising providing a single use delivery device having a manually deformable liquid container, a tip projecting from an outlet on the distal end of the container and being in fluid communication with the inner chamber of the container, a primer element for collapsing a portion of the deformable container for driving air out of said chamber by depressing the primer element, and a one-way valve disposed between the tip and the deformable container as described herein; providing a vascular access device having a proximal end, a distal end, and a passageway therethrough, the proximal end having a female luer tip in fluid communication with the passageway; placing the distal end of the vascular access device in a blood vessel of a patient; depressing the primer element to evacuate air within the chamber; engaging the male luer connector of the container with the female luer of the vascular access device; applying force to deform the container so that a solution located in the chamber flows through the one-way valve into the vascular access device; and disengaging the male luer connector of the container from the female luer of the vascular access device.

BRIEF DESCRIPTION OF THE DRAWINGS

FIG. 26 is a perspective view illustrating a fifth embodiment of the single use pre-filled delivery device of the present invention.

DETAILED DESCRIPTION OF THE INVENTION

Figure 1:
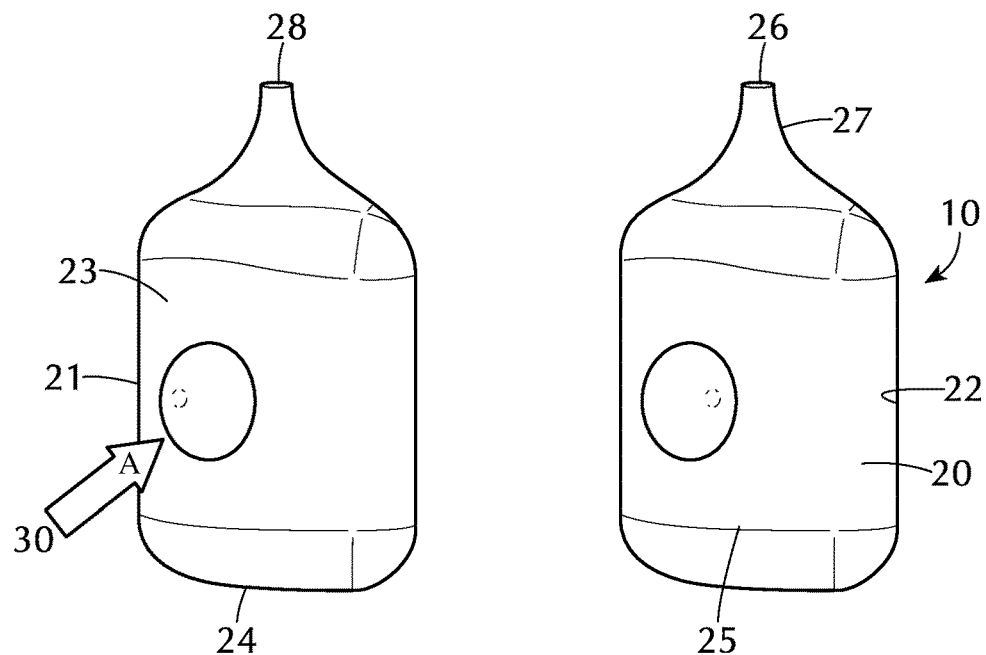
FIG. 1 is a perspective view illustrating one embodiment of the single use pre-filled delivery device of the present invention.

Before describing several exemplary embodiments of the invention, it is to be understood that the invention is not limited to the details of construction or process steps set forth in the following description. The invention is capable of other embodiments and of being practiced or being carried out in various ways.

In this disclosure, a convention is followed wherein the distal end of the device is the end closest to a patient and the proximal end of the device is the end away from the patient and closest to a practitioner.

The term "deformable" refers to a wall or container that is structured to be flexible enough to collapse at least partially into the inner chamber under manual depression. The shape and extent of the deformation will vary with the various configurations of the inner chamber and deformable container.

As used herein, the term "luer" with respect to a connector, connection or tip refers to a connection collar that is the standard way of attaching syringes, catheters, hubbed needles, IV tubes, etc. to each other. The luer connection consists of male and female interlocking tubes, slightly tapered to hold together better with even just a simple pressure/twist fit. Luer connectors can optionally include an additional outer rim of threading, allowing them to be more secure. The luer connector male end is generally associated with a flush assembly and can interlock and connect to the female end located on a vascular access device (VAD). A luer connector comprises a distal end, a proximal end, an irregularly shaped outer wall, a profiled center passageway for fluid communication from the chamber of the barrel of a syringe to the hub of a VAD. A luer connector also has a distal end channel that releasably attaches the luer connector to the hub of a VAD, and a proximal end channel that releasably attaches the luer connector to the barrel of a syringe.

The term "priming" is defined as the removal of one or more air bubbles. In the present invention, the volume of the collapsible priming element matches or exceeds the volume of the air bubbles within the device. All regions of the device collapse to minimize dead space remaining in the delivery device after use.

One application where a primer element is be useful is that of a device prefilled with saline or medication and intended for direct connection with a vascular access device (VAD). This type of pre-filled device often requires the incorporation of one or more air bubbles within the internal volume of the container. It is crucial that these devices contain no air when connected to the VAD. Therefore a priming step must be incorporated into the workflow prior to attachment to the VAD.

The present invention overcomes problems associated with known fluid administration devices and flush devices by providing a single use pre-filled delivery device that effectively removes air and/or solution from a closed container in a step called "priming". This priming step is achieved through a collapsible deformable container and primer element as described below.

A single use sterile delivery device overcomes problems found with the prior art by reducing the risk associated with contamination due to manually filling a syringe with solution from a vial. Other advantages of this invention over prior art include the following: a) the device of the present invention is capable of a generating a secure connection with a receiving needleless female vascular access connector and b) the single use sterile delivery device of the present invention incorporates a deformable and collapsible feature capable of displacing a volume comparable to the volume of the contained air bubbles allows the syringe to be primed prior to use.

The single use pre-filled delivery device of the present invention is shown in FIGS. 1-5. A single use sterile delivery device of the present invention reduces the risk associated with contamination due to manual filling a syringe with flush solution, drug or medicament from a vial. Generally speaking, the single use device of the present invention capable of delivering sterile solution to the female luer connection of a VAD. In general, the device comprises a deformable container capable of holding between 0.5 mL and 10 mL of sterile.

Referring to FIG. 1, a single use pre-filled delivery device 10 according to the present invention generally comprises a manually deformable container 20 including a side wall 21 having an inside surface 22 defining a chamber 23 for retaining fluid, and a primer element 30 for removing one or more air bubbles from the chamber 23. The deformable container 20 further comprises a closed proximal end 24, a body 25 and an open distal end 26 including a tip 27 having a passageway 28 therethrough providing fluid communication with the chamber 23. Thus, the delivery device 10 of the present invention is capable of a generating a secure connection with a receiving needleless female vascular access connector. The tip 27 of the deformable container 20 may includes a male luer connector that enables secure connection to the female luer connector within a VAD. The vascular access device may be a syringe, extension set, intravenous set, stop cock, tubing, high pressure extension tubing, or needleless connector.

The primer element 30 is attached to and in fluid communication with the deformable container 20. The primer element 30 may be assembled into the body 25 of the container 20 or it may be molded into the body 25 of the container 20. The primer element 30 may be positioned on the proximal end 24 of the container 20.

In the present invention, the volume of the collapsible priming element matches or exceeds the volume of the air bubbles within the device. All regions of the device collapse to minimize dead space remaining in the delivery device after use.

As shown in FIG. 1, the primer element 30 may be in the form of a collapsible button which is convex prior to the primer being manually depressed in the direction shown by arrow "A" and is concave after the primer is manually depressed. As shown in FIG. 1, a convex shape is molded into the surface of the deformable container 20. Activation or priming is achieved by depressing on the convex surface to create a concave surface. The primer element 30 when activated, displaces a specific volume within the container. The displaced volume matches or exceeds the volume of the air bubbles initially contained within the chamber 23 of the container 20. The primer element 30 may be either molded or assembled in the body of the deformable container 20. A container 20 containing both air and liquid may be positioned such that the air is located in the region of the open distal end 26 of container 20 and the liquid is positioned away from the outlet. The primer element 30 may be positioned away from the open distal end 26 of container 20, such that when activated, the button preferentially expels air over liquid.

Figure 2:
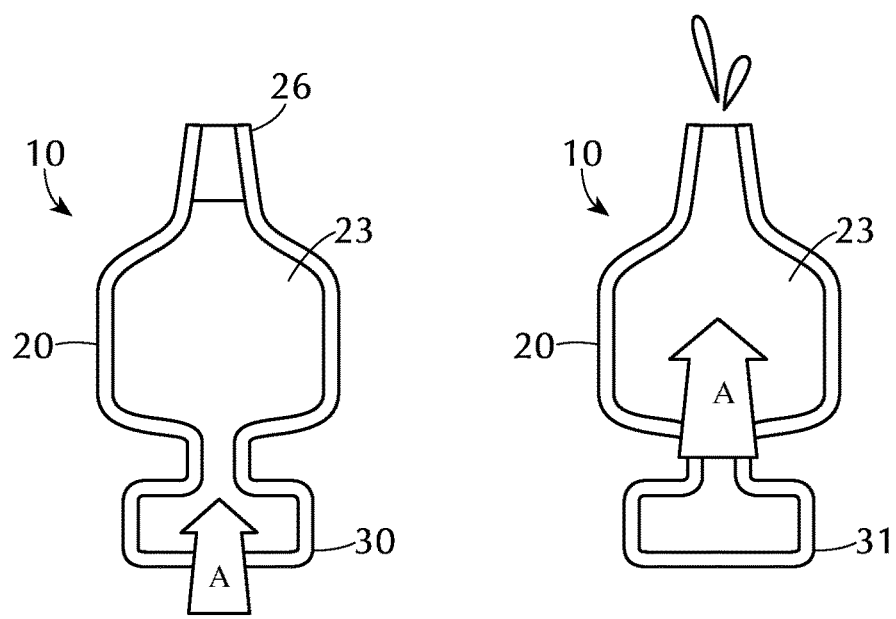
FIG. 2 is a perspective view illustrating a second embodiment of the single use pre-filled delivery device of the present invention.
Figure 3:
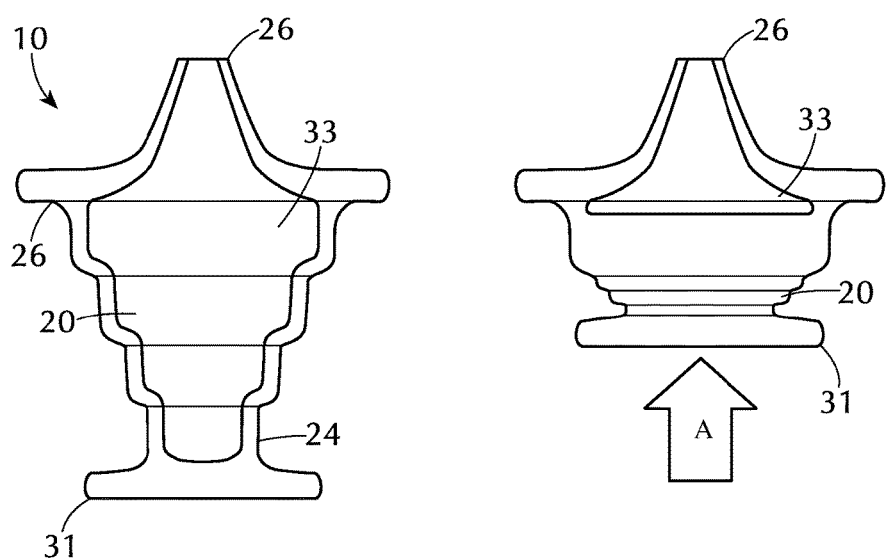
FIG. 3 is a perspective view illustrating a third embodiment of the single use pre-filled delivery device of the present invention.
Figure 4:
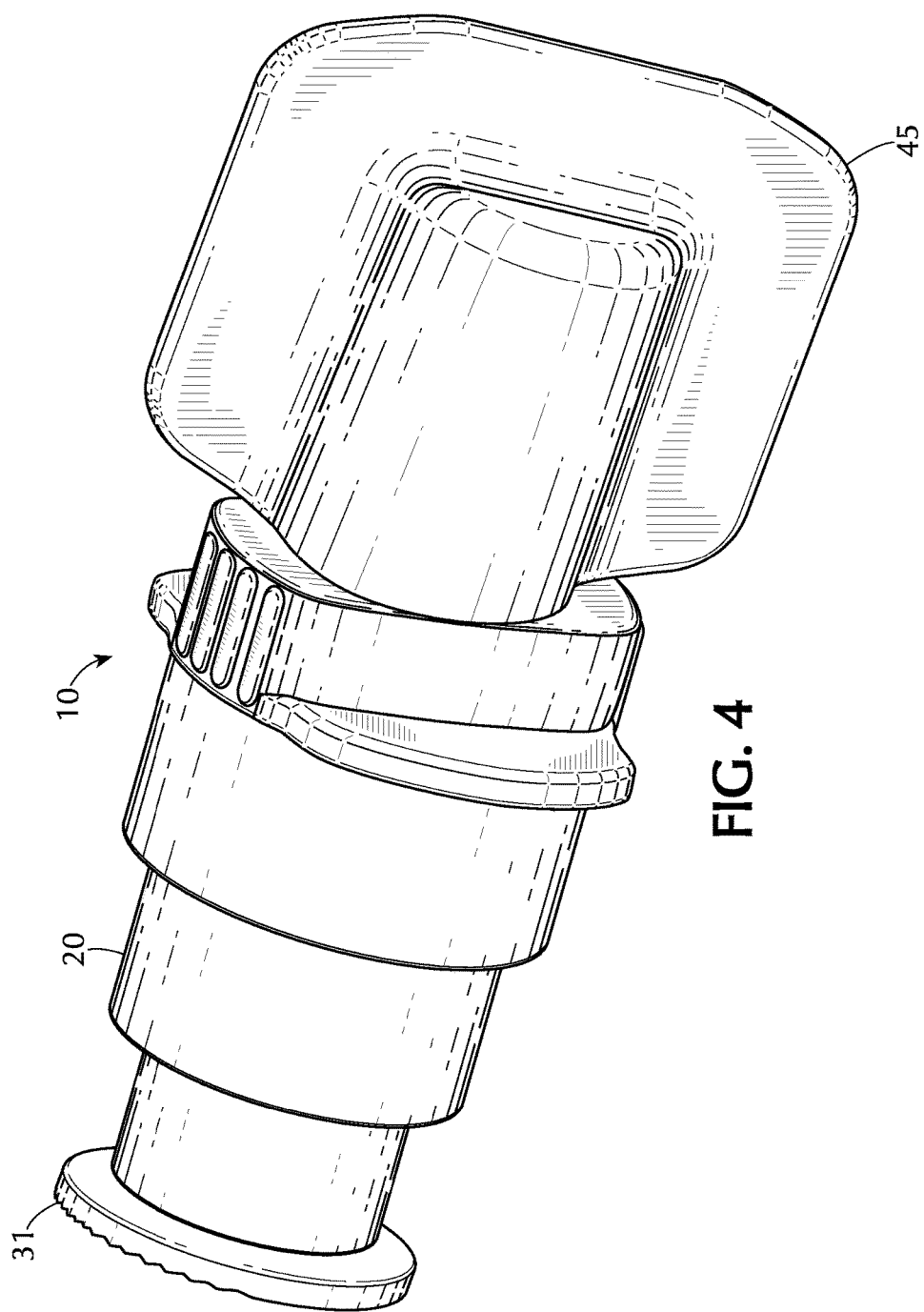
FIG. 4 is a perspective view illustrating a third embodiment of the single use pre-filled delivery device of the present invention having a tip cap.
Figure 5:
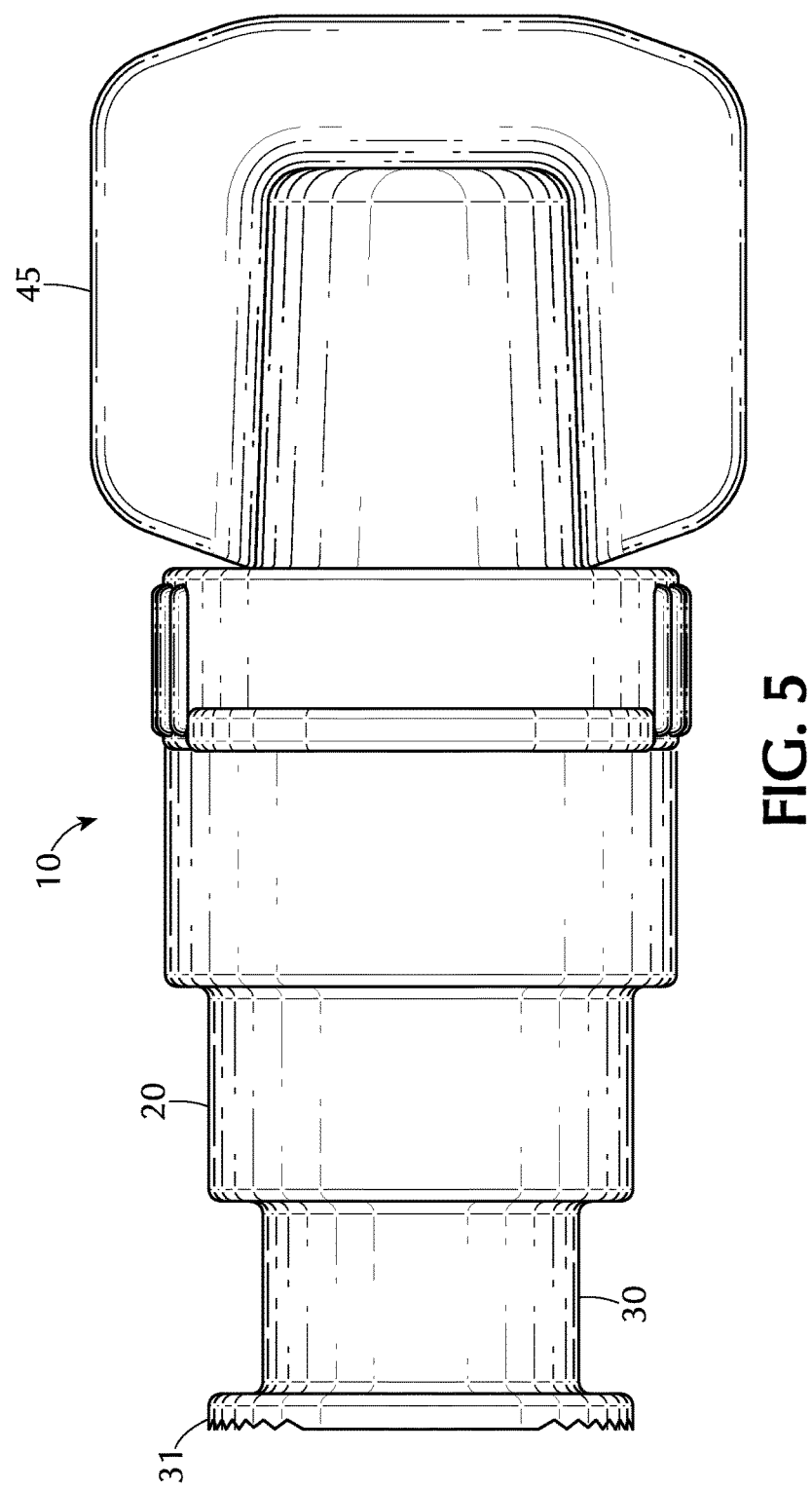
FIG. 5 is a top view illustrating a third embodiment of the single use pre-filled delivery device of the present invention having a tip cap.
Figure 6:
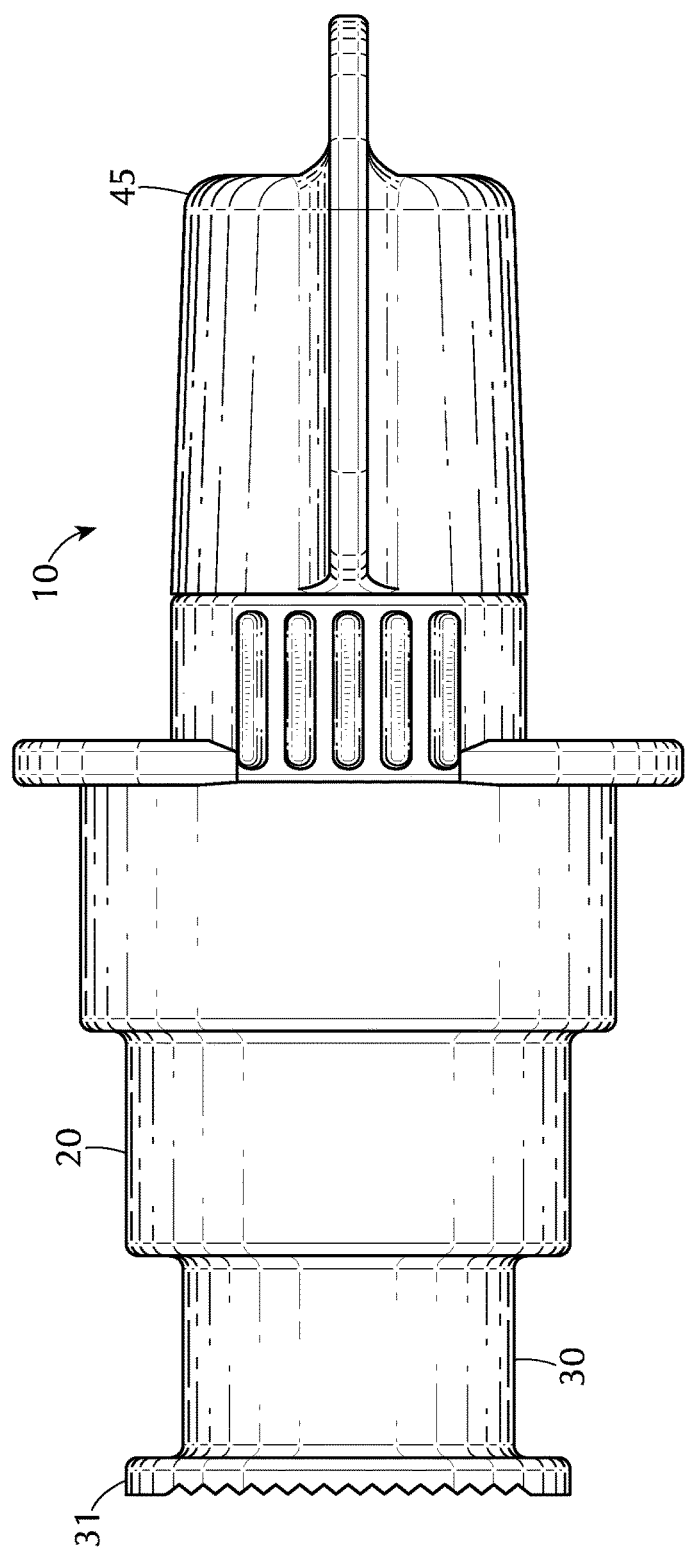
FIG. 6 is a side view illustrating a third embodiment of the single use pre-filled delivery device of the present invention having a tip cap.
Figure 7:
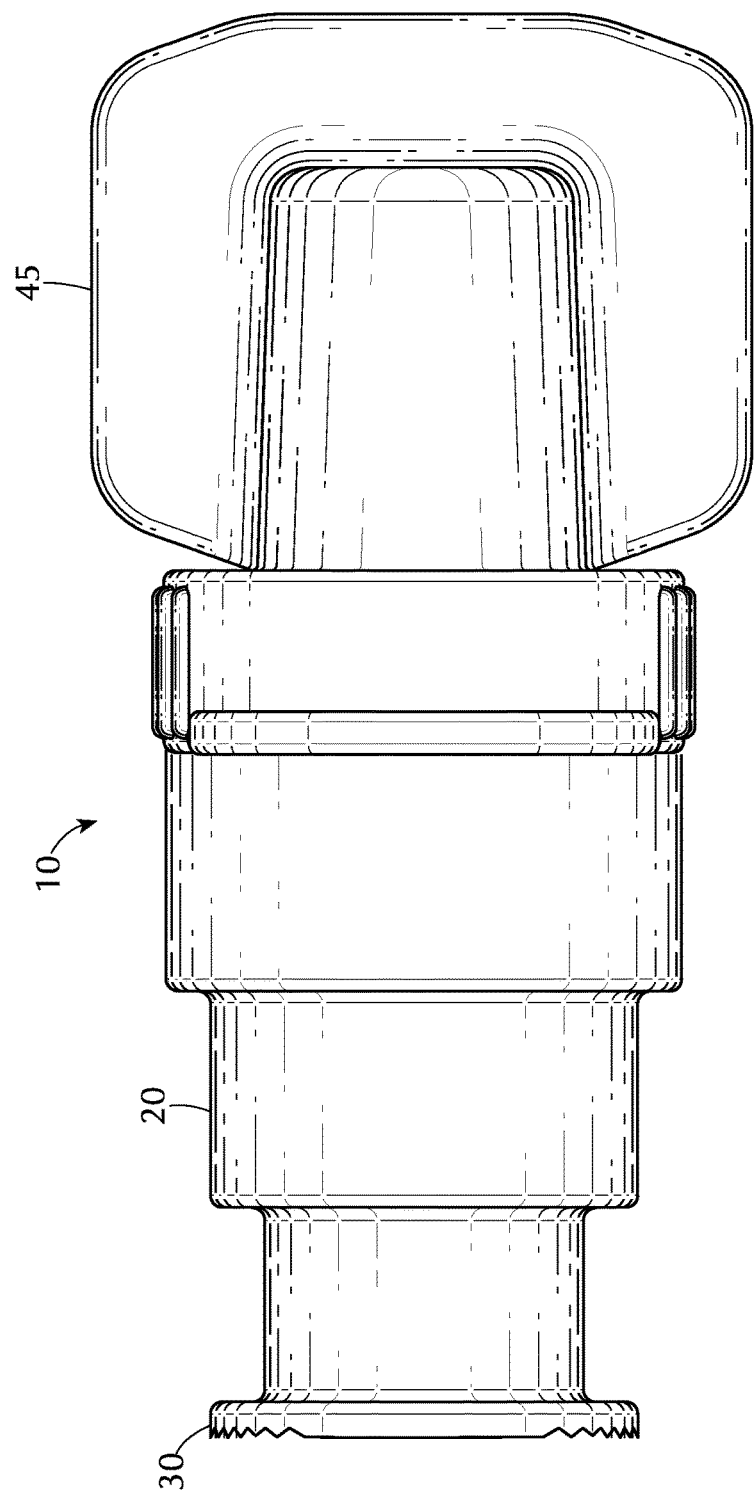
FIG. 7 is a bottom view illustrating a third embodiment of the single use pre-filled delivery device of the present invention having a tip cap.
Figure 8:
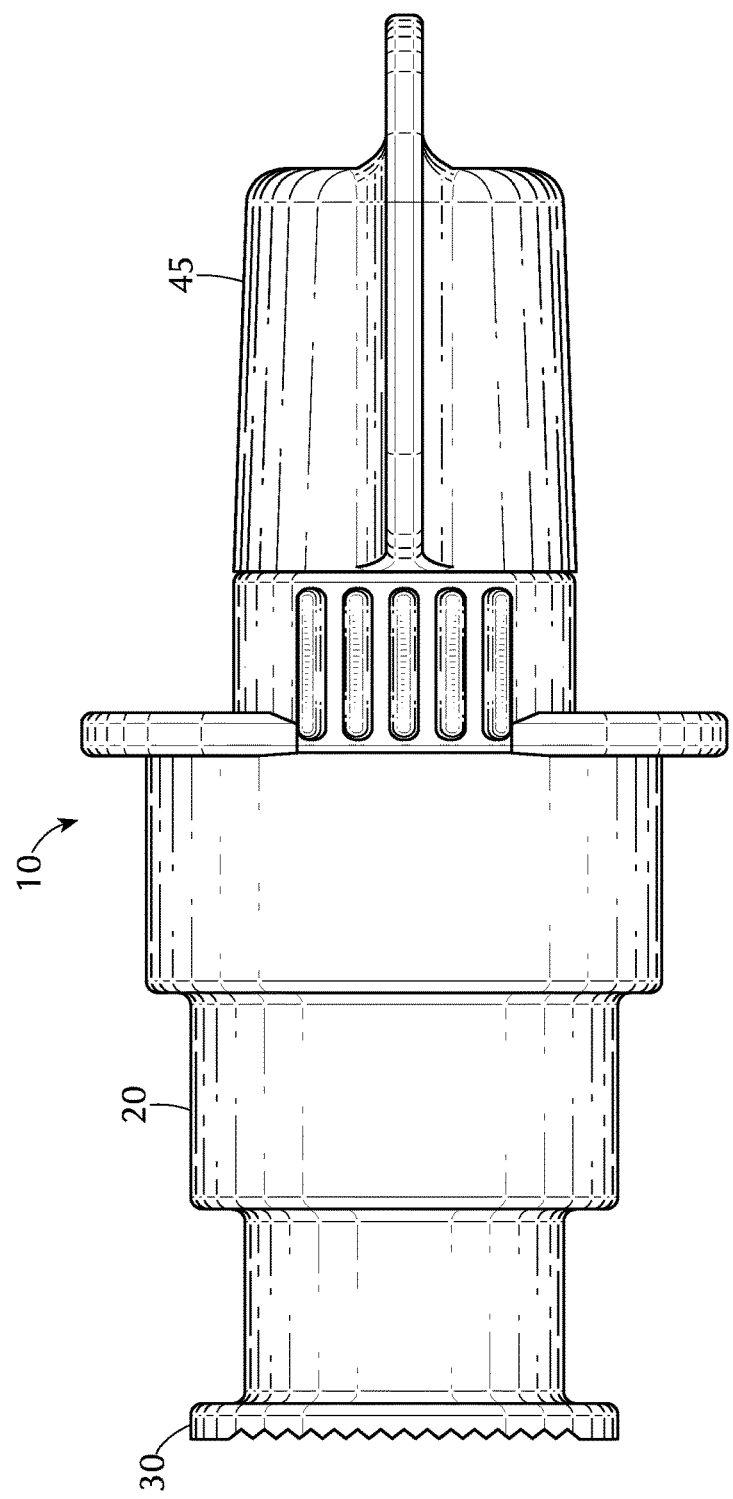
FIG. 8 is a side view illustrating a third embodiment of the single use pre-filled delivery device of the present invention having a tip cap.
Figure 10:
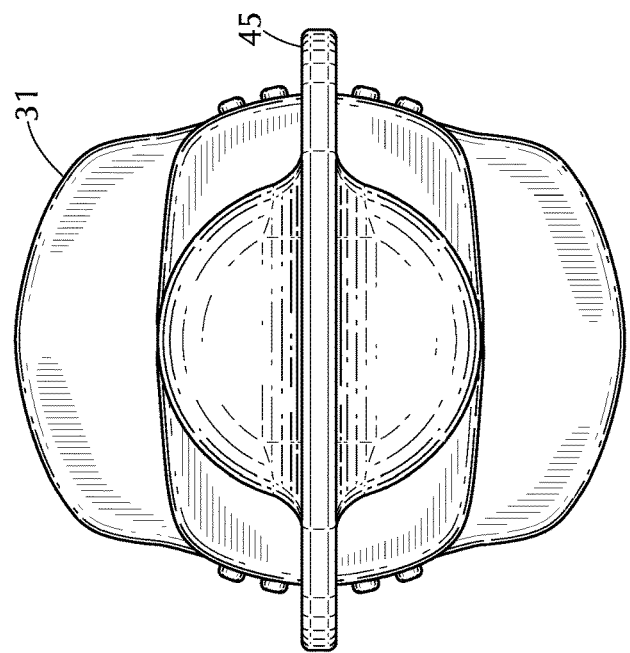
FIG. 10 is a front view illustrating a third embodiment of the single use pre-filled delivery device of the present invention having a tip cap.
Figure 9:
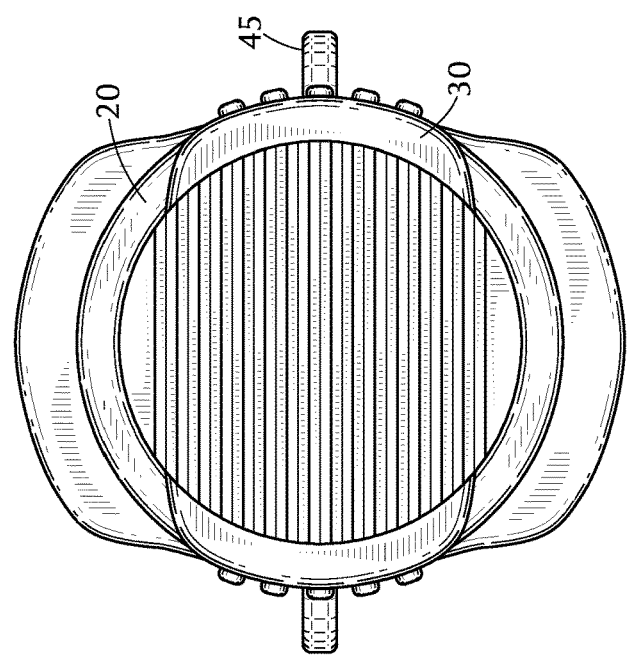
FIG. 9 is a back view illustrating a third embodiment of the single use pre-filled delivery device of the present invention having a tip cap.
Figure 11:
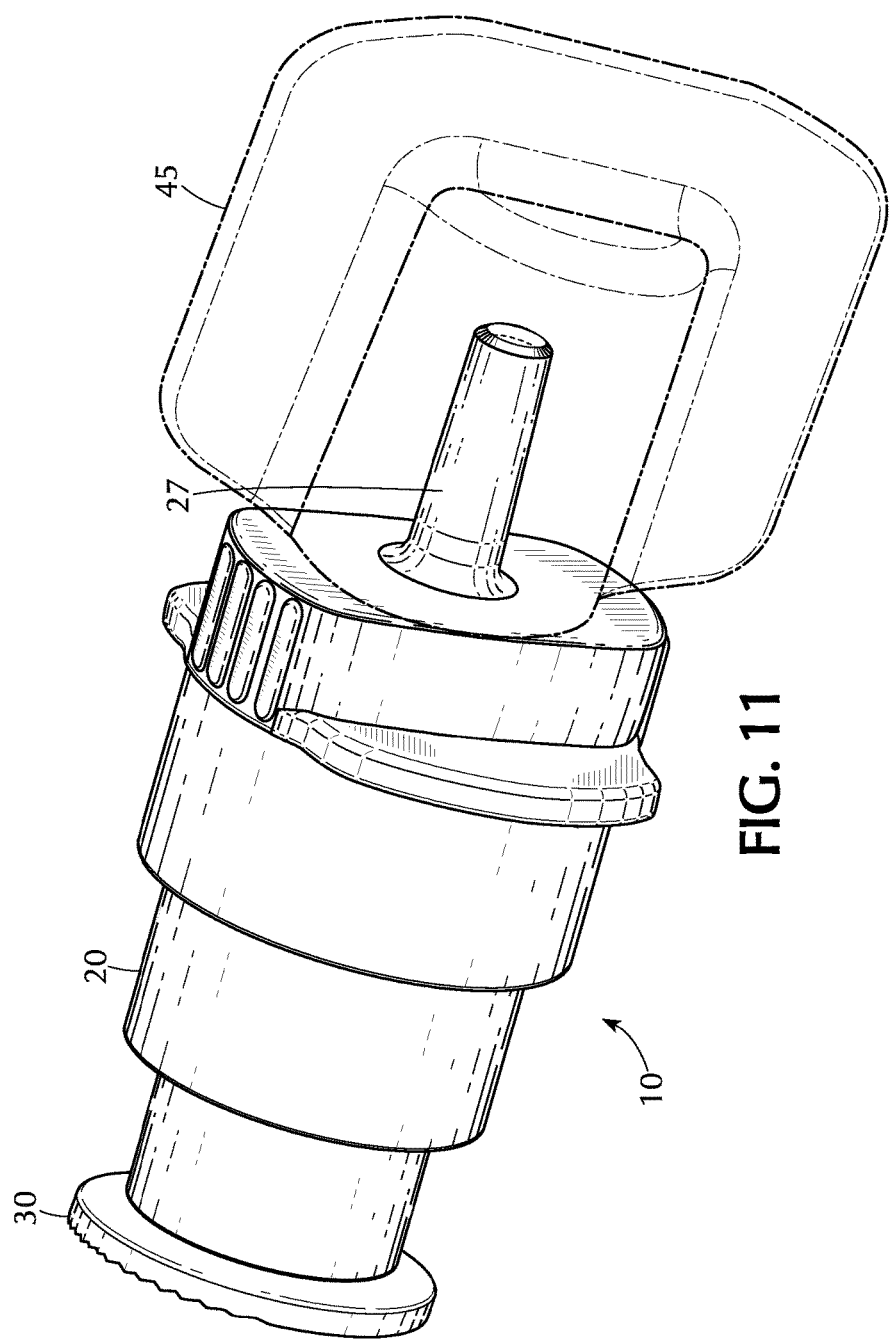
FIG. 11 is a perspective view illustrating a third embodiment of the single use pre-filled delivery device of the present invention having a tip cap.
Figure 12:
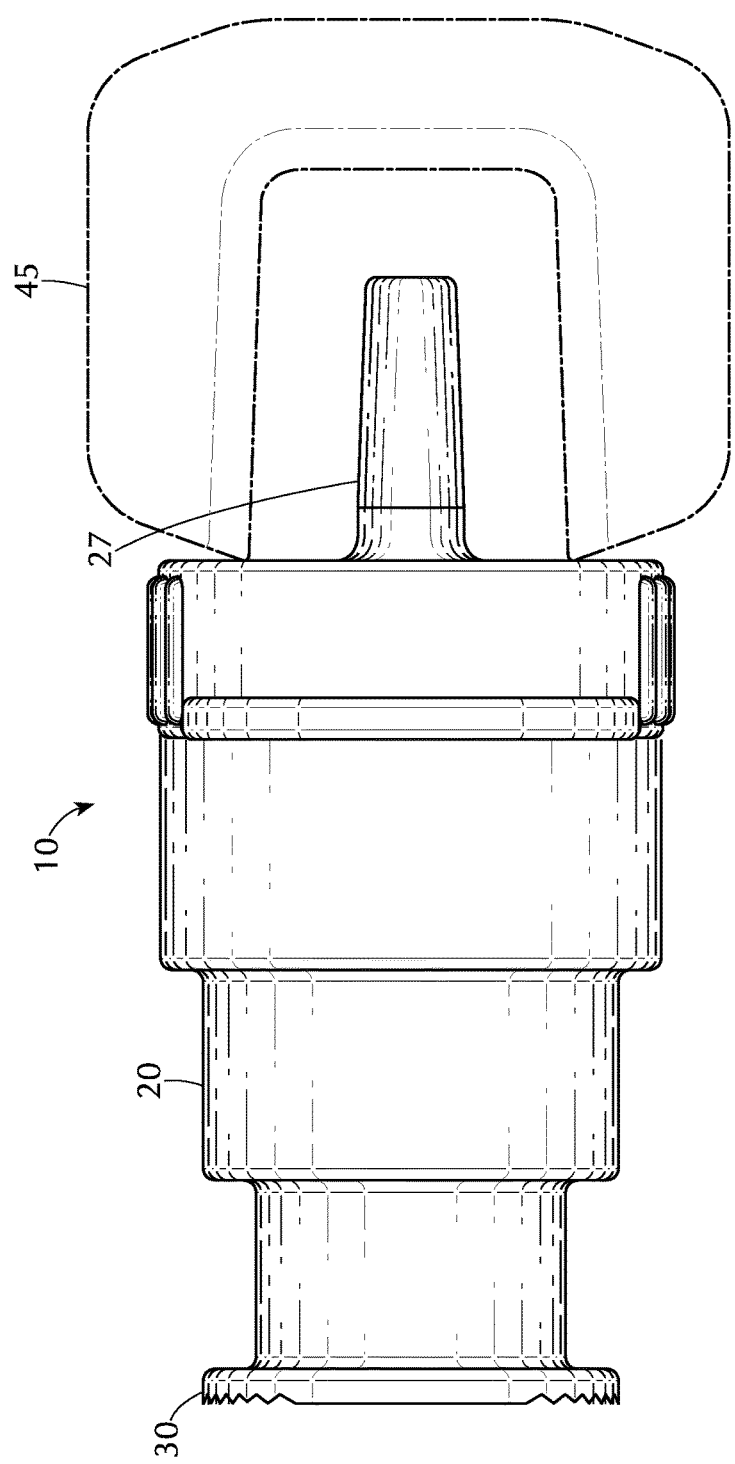
FIG. 12 is a top view illustrating a third embodiment of the single use pre-filled delivery device of the present invention having a tip cap.
Figure 13:
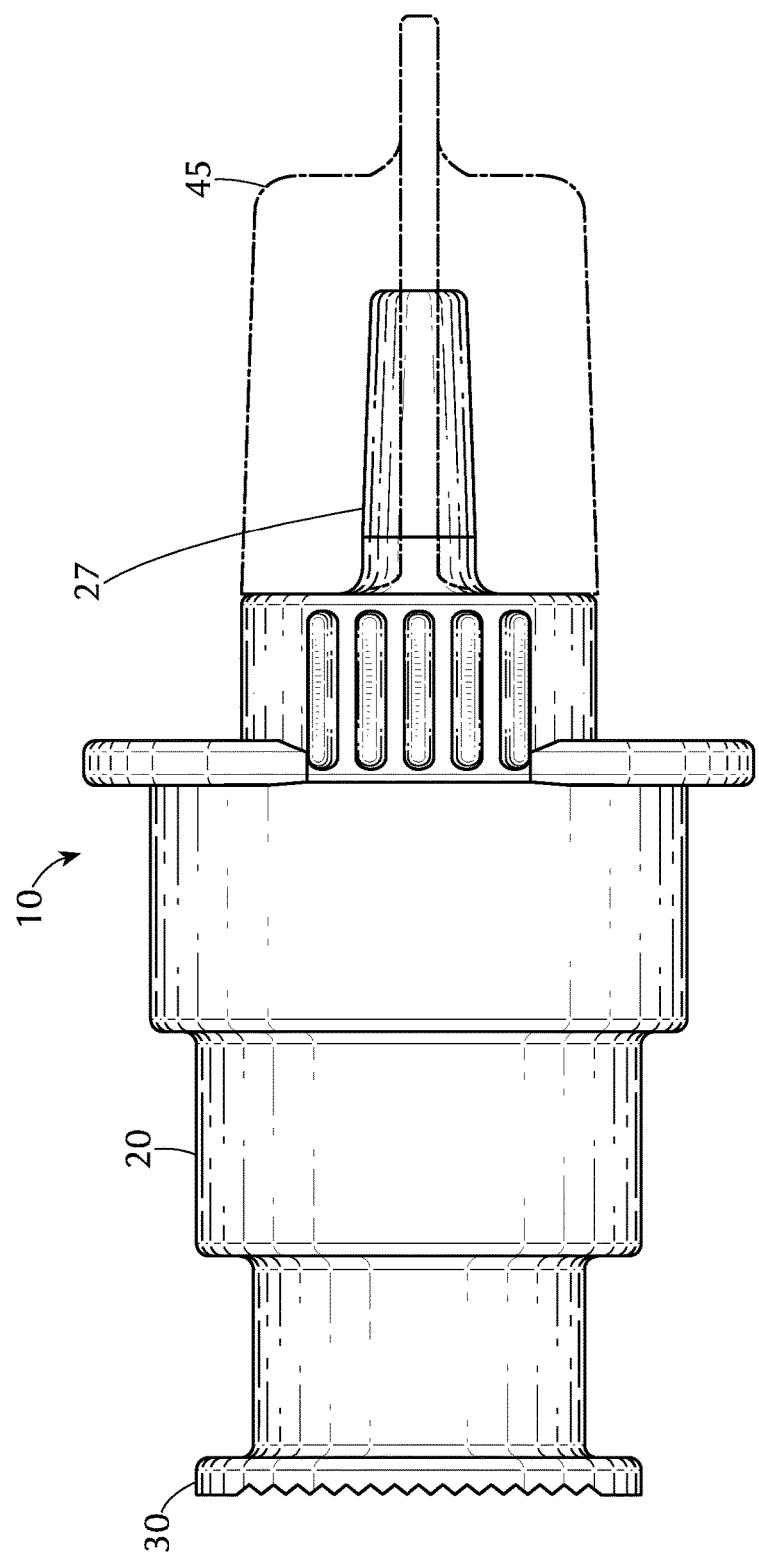
FIG. 13 is a side view illustrating a third embodiment of the single use pre-filled delivery device of the present invention having a tip cap.
Figure 14:
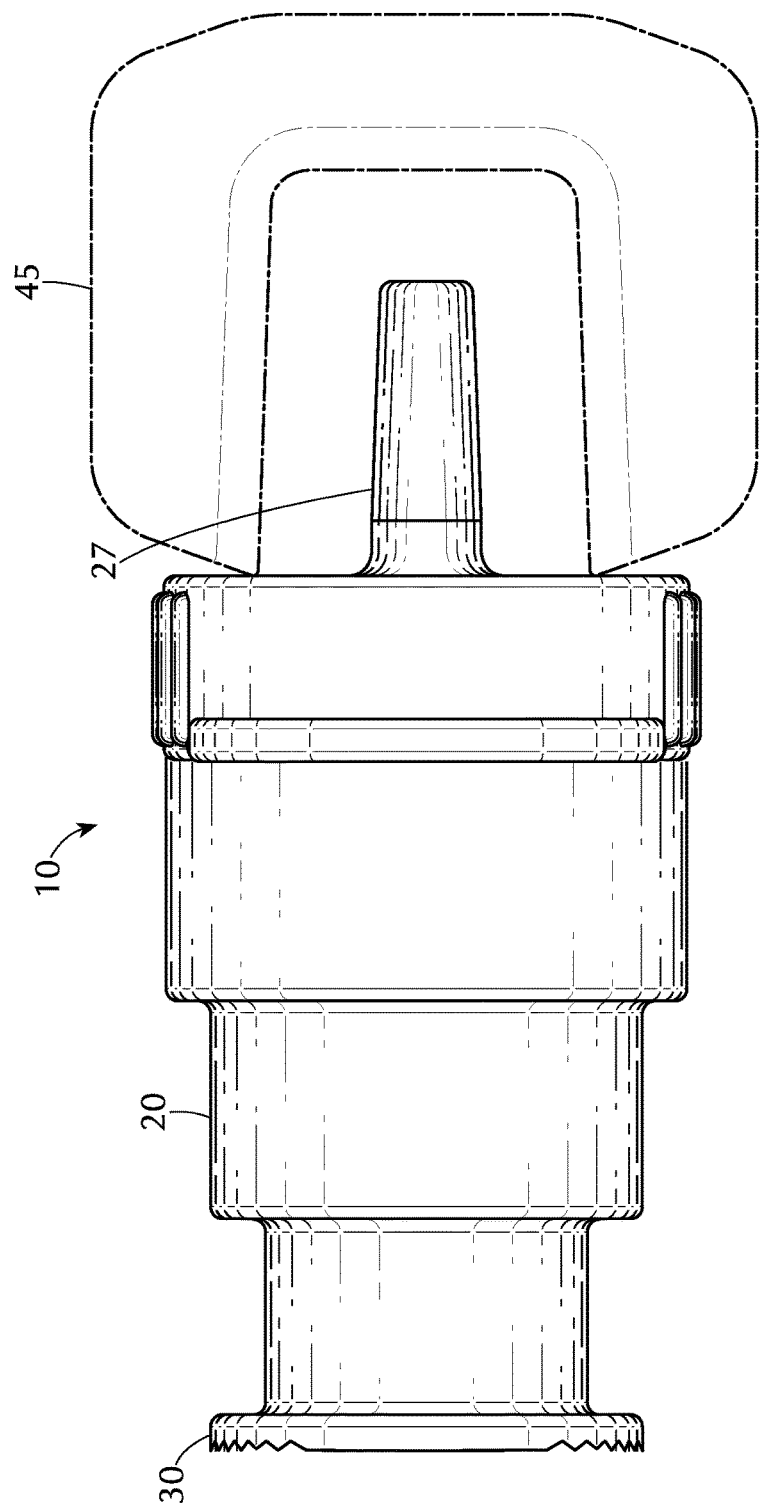
FIG. 14 is a bottom view illustrating a third embodiment of the single use pre-filled delivery device of the present invention having a tip cap.
Figure 15:
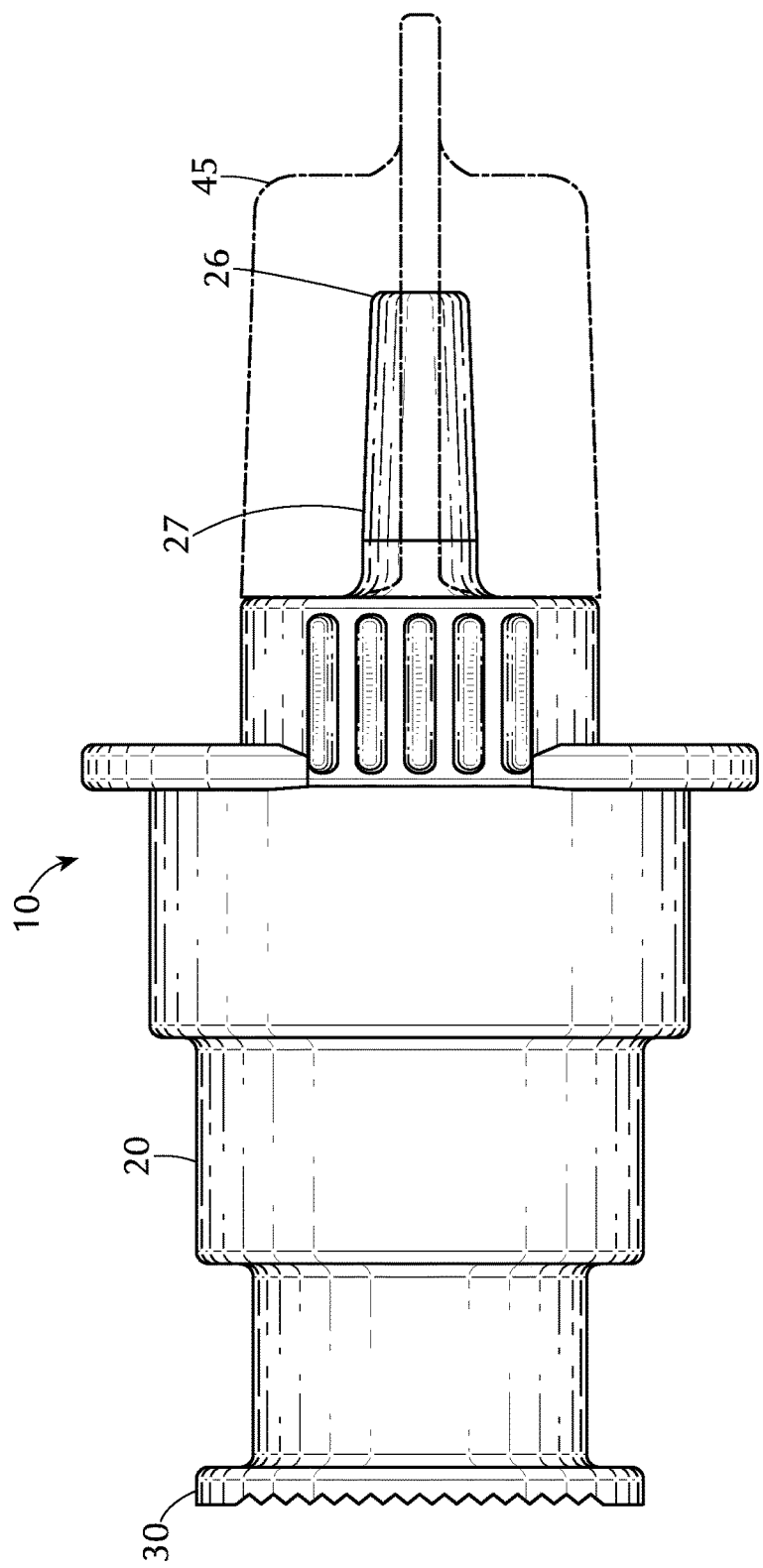
FIG. 15 is a side view illustrating a third embodiment of the single use pre-filled delivery device of the present invention having a tip cap.
Figure 17:
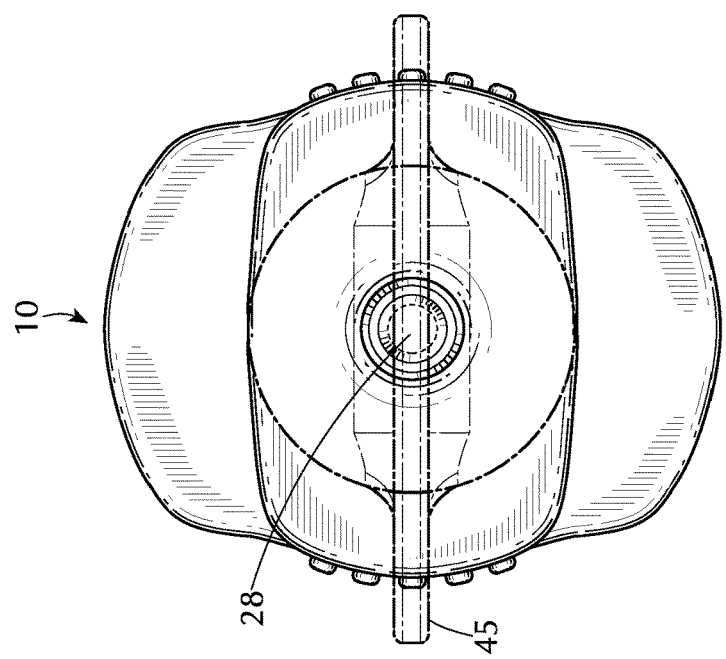
FIG. 17 is a front view illustrating a third embodiment of the single use pre-filled delivery device of the present invention having a tip cap.
Figure 16:
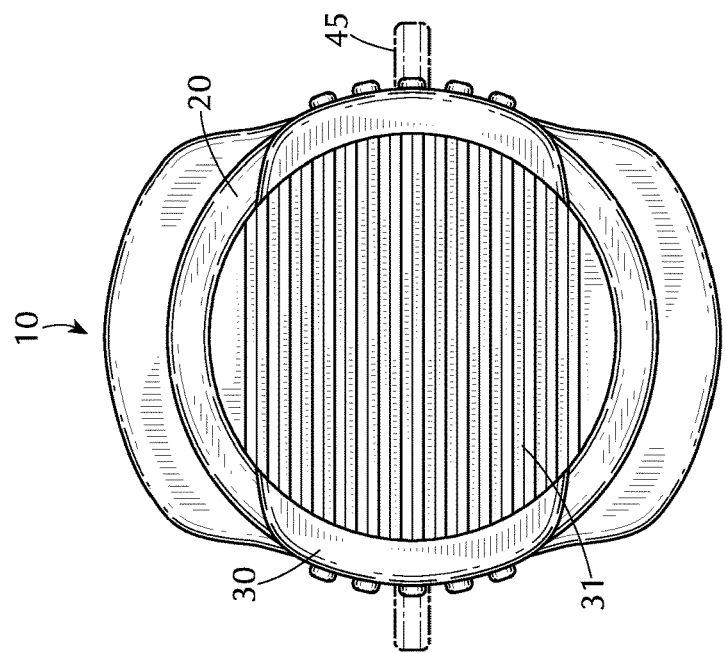
FIG. 16 is a back view illustrating a third embodiment of the single use pre-filled delivery device of the present invention having a tip cap.
Figure 18:
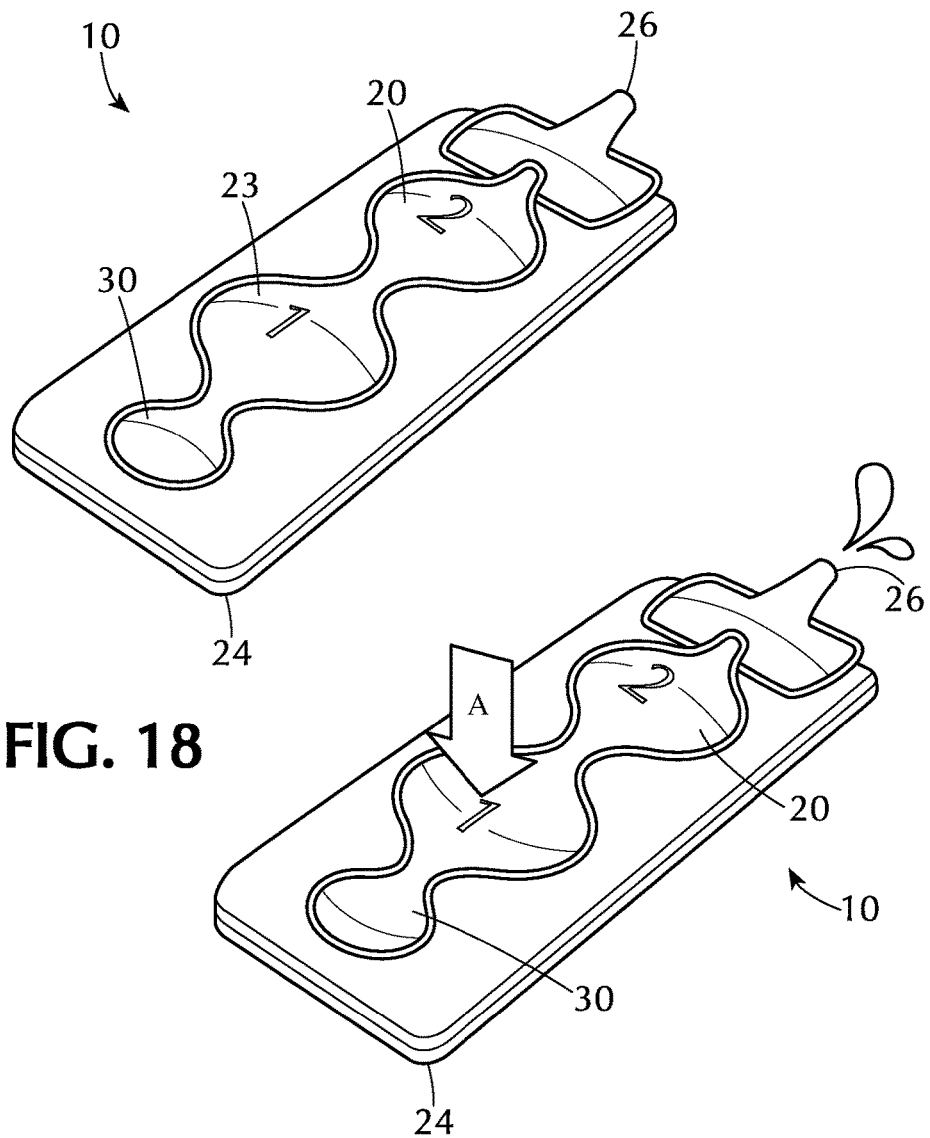
FIGS. 18 and 19 are perspective views illustrating a fourth embodiment of the single use pre-filled delivery device of the present invention.
Figure 19:
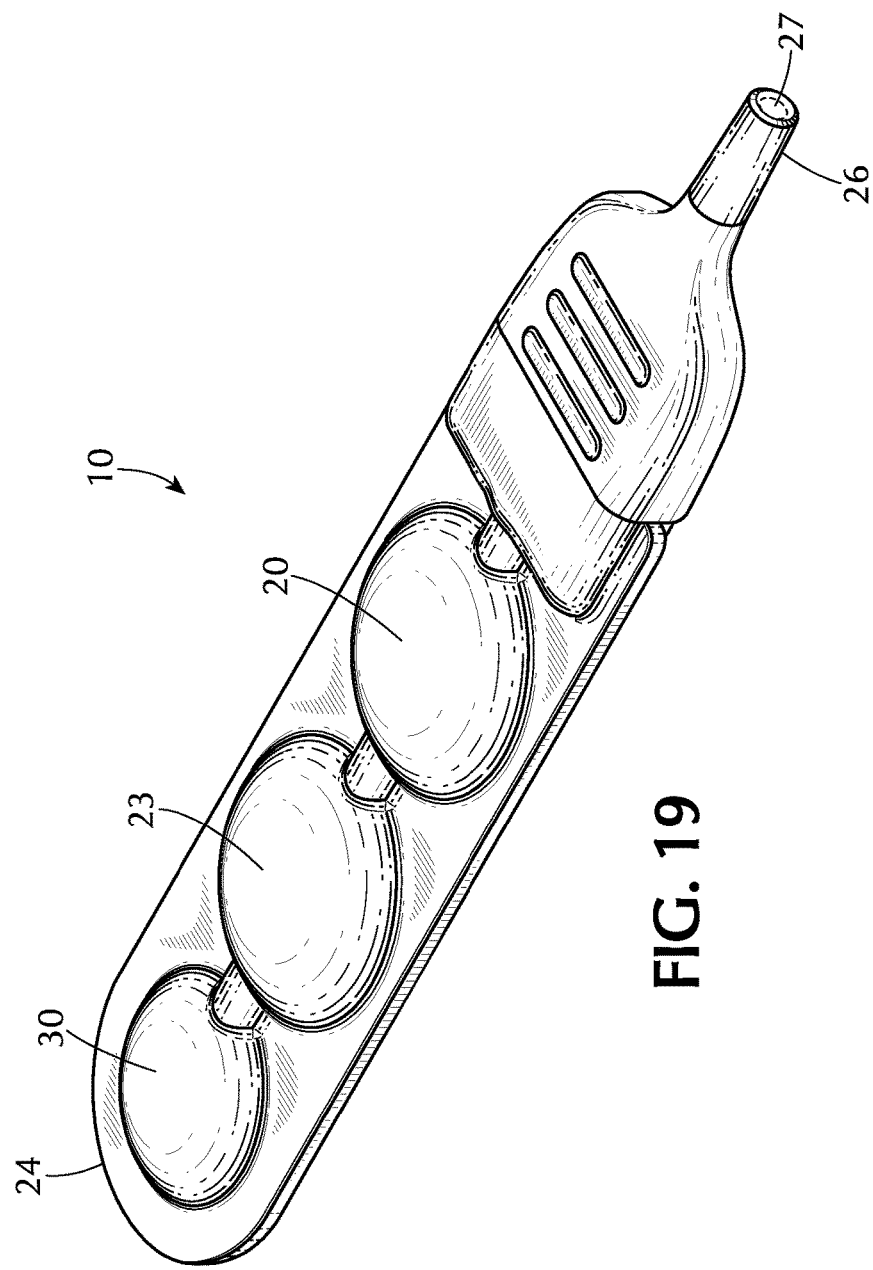
Figure 20:
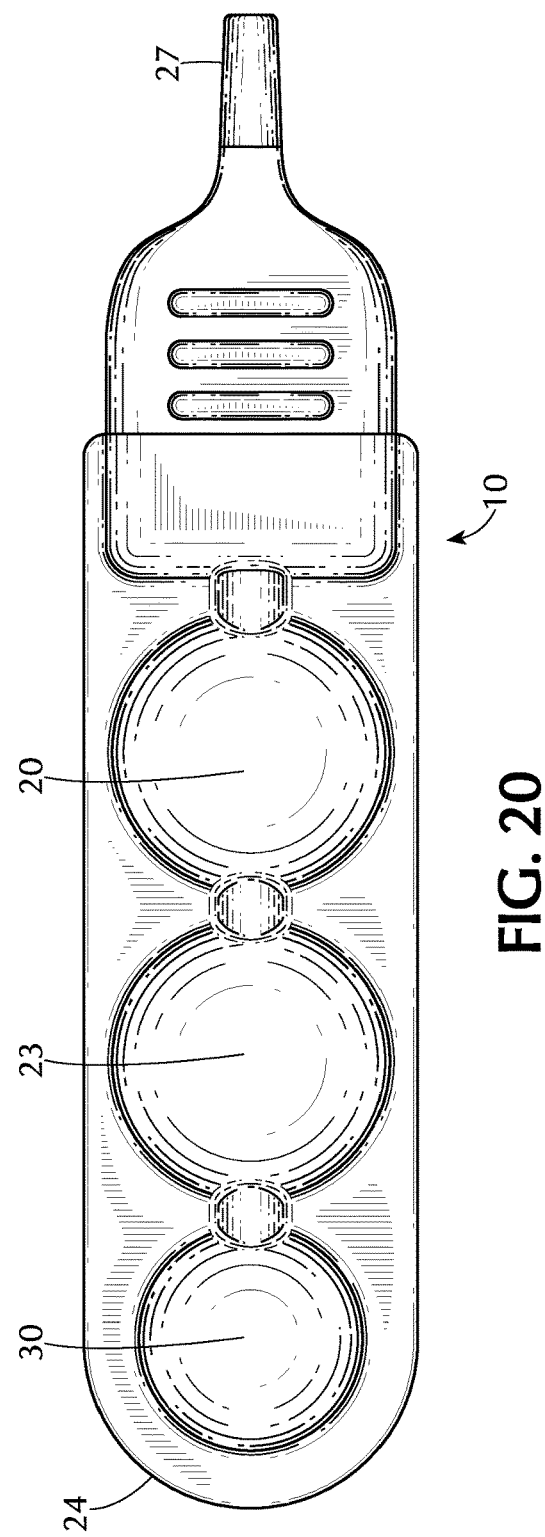
FIG. 20 is a top view illustrating a fourth embodiment of the single use pre-filled delivery device of the present invention.
Figure 21:
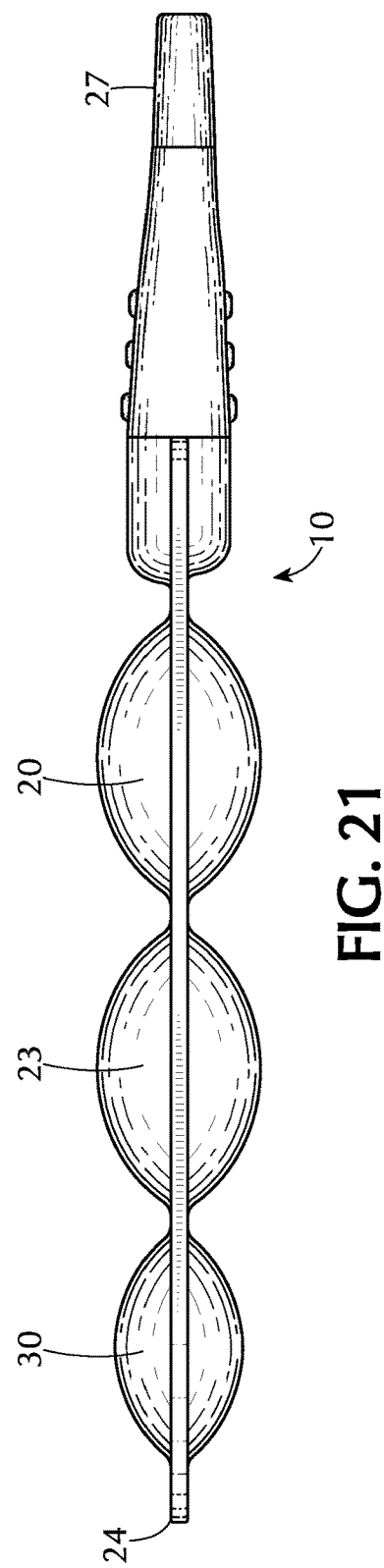
FIG. 21 is a side view illustrating a fourth embodiment of the single use pre-filled delivery device of the present invention.
Figure 22:
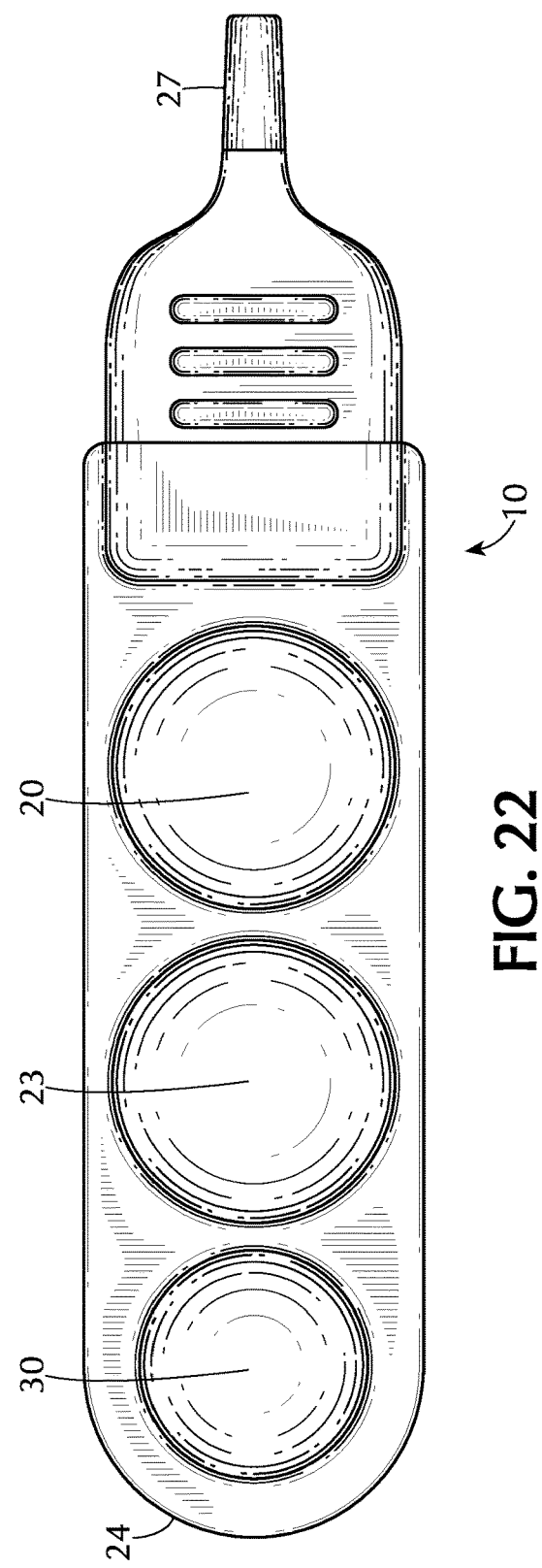
FIG. 22 is a bottom view illustrating a fourth embodiment of the single use pre-filled delivery device of the present invention.
Figure 23:
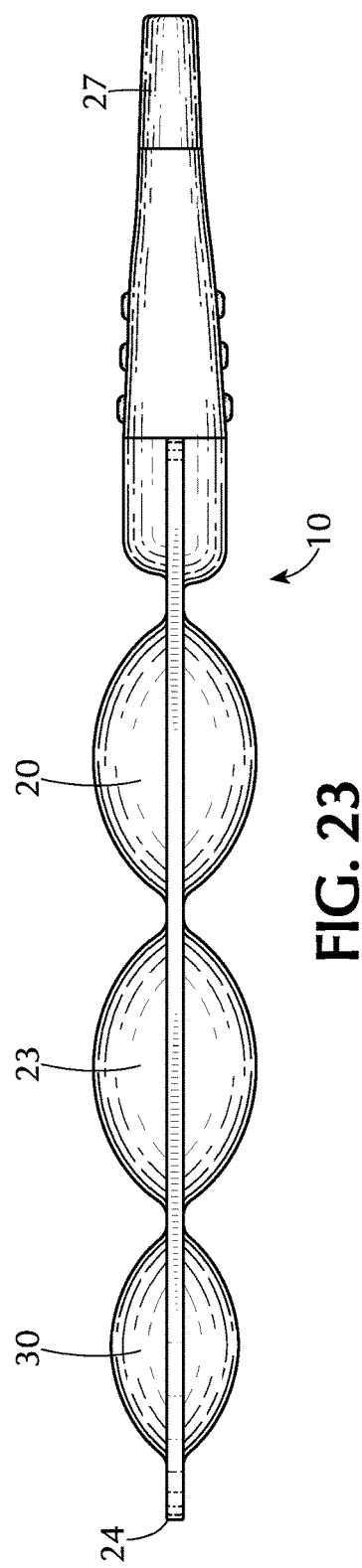
FIG. 23 is a side view illustrating a fourth embodiment of the single use pre-filled delivery device of the present invention.
Figure 25:
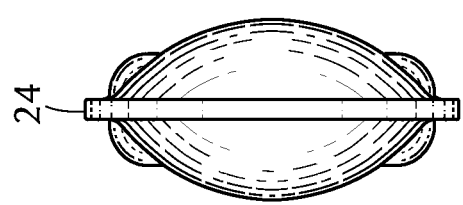
FIG. 25 is a back view illustrating a fourth embodiment of the single use pre-filled delivery device of the present invention.
Figure 24:
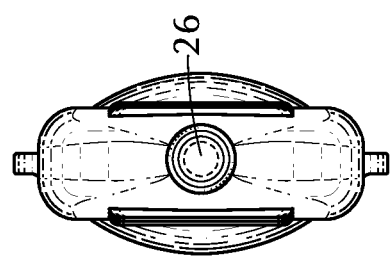
FIG. 24 is a front view illustrating a fourth embodiment of the single use pre-filled delivery device of the present invention.

As shown in FIGS. 2 and 3, the primer element 30 may include a thumb press 31 located at the proximal end 24 of the container 20 which may be manually depressed in the direction shown by arrow "A". As shown in FIGS. 3-17, the body 25 of the container 20 may comprise a plurality of collapsible funnel-shaped, concentrically-arranged side walls, wherein the diameters of the concentrically-arranged walls decrease from the distal end 26 to the proximal end 24 of the liquid container 20. The shape of the body of the deformable container allows a portion of the device 10 to fold in onto its self, displacing a prescribed portion of the contents of the inner chamber 23 and matching the volume required to prime the syringe.

In an alternate embodiment, the primer element 30 includes a thumb press 31 located at the proximal end 24 of the container 20 and the body 25 of the container 20 comprises a plurality of collapsible funnel-shaped, nonconcentrically-arranged side walls, wherein the diameters of the nonconcentrically-arranged walls decrease from the distal end 26 to the proximal end 24 of the liquid container 20.

Another embodiment of the present invention is directed to a single use delivery device 10 including a manually deformable liquid container 20 defining two or more inner chambers 23, the container 20 having a distal end 26, a proximal end 24, and an outlet on the distal end 26; a tip 27 projecting from the outlet on the distal end 26 of the container 20, the tip 27 in fluid communication with the inner chamber 23 of the container 20; a primer element 30 for collapsing a portion of the deformable container 20 for driving air out of said chamber 23 by depressing the primer element 30, said primer element 30 being attached to the deformable container 20. As shown in FIGS. 18-25, the primer element 30 may be in the form of a series of two or more adjoining collapsible buttons in fluid communication to the luer end. The two or more adjoining collapsible buttons may be connected to the luer end either in series or in parallel, as shown in FIGS. 18-25. The two or more adjoining collapsible buttons are activated by pressing down in the direction shown by arrow "A" on the convex surface to collapse the volume within and expelling the remaining contents from the luer end. When the device is held with the luer end at the highest point, the one or more air bubbles will move to the luer end. In this position, collapsing the two or more adjoining collapsible buttons will expel air from the device such that the remaining inner volume of the device comes in contact with the fluid.

In one or more embodiments, the single use delivery device 10 includes a pre-selected amount of fluid in the chamber 23.

The deformable container 20 may be made of thermoplastic elastomers.

As shown in FIG. 26, another embodiment of the present invention is directed to a single use delivery device 10 including a manually deformable liquid container 20 defining one or more inner chambers 23, the container 20 having a distal end 26, a proximal end 24, and an outlet on the distal end 26; a tip 27 projecting from the outlet on the distal end 26 of the container 20, the tip 27 in fluid communication with the inner chamber 23 of the container 20; a primer element 30 for collapsing a portion of the deformable container 20 for driving air out of said chamber 23 by depressing the primer element 30 in the direction shown by arrow "A", said primer element 30 being attached to the deformable container 20; and a one-way valve 55 disposed between the tip 27 and the deformable container 20, the one-way valve in fluid communication with the inner chamber 23 of the container 20, said one-way valve permitting air or fluid evacuation from the inner chamber 23 but preventing air or fluid intake into the inner chamber 23 when the container 20 is manually deformed and released. Another embodiment incorporates one way valves at connection points between individual chambers or between the chambers and the luer end. The one-way valve may be a duckbill valve, an umbrella valve, a ball-check valve, diaphragm check valve, swing check valve, stop-check valve, lift-check valve or a combination thereof. The use of incorporated valves reduces flow back into the device from the luer connection point. This feature reduces reflux in the VAD path generated by back pressure within the syringe. An incorporated valve may also be used to reduce flow between chambers. One example is a case where a valve is positioned between a chamber used to prime the syringe and a chamber containing the intended contents for delivery.

Another embodiments of the present invention is directed to a method of delivery fluid to a vascular access device comprising providing a single use delivery device 10 having a manually deformable liquid container 20 defining an inner chamber 23, the container 20 having a distal end 26, a body 25, a proximal end 24, and an outlet on the distal end 26; a tip 27 projecting from the outlet on the distal end 26 of the container 20, the tip 27 in fluid communication with the inner chamber 23 of the container 20; and a primer element 30 for removing one or more air bubbles from the chamber 23, said primer element 30 being attached to and in fluid communication with the deformable container 20; providing a vascular access device having a proximal end, a distal end, and a passageway therethrough, the proximal end having a female luer tip in fluid communication with the passageway; placing the distal end of the vascular access device in a blood vessel of a patient; depressing the primer element 30 to evacuate air within the chamber 23; engaging the male tip 27 of the container 20 with the female tip of the vascular access device; applying force to deform the container 20 so that a solution located in the chamber 23 flows through the one-way valve into the vascular access device; and disengaging the male tip 27 of the container 20 from the female tip of the vascular access device.

The one-way valve prevents reflux of solution in the passageway 28. The one-way valve may be a duckbill valve, an umbrella valve, a ball-check valve, diaphragm check valve, swing check valve, stop-check valve, lift-check valve or a combination thereof.

The delivery device 10 of the present invention may be used in conjunction with a vascular access device having a proximal end, a distal end and a passageway 28 therethrough, said proximal end having a female luer tip in fluid communication with said passageway 28. To use the delivery device 10 in a flushing procedure or to administer a fluid, the user engages the male luer tip 27 of the deformable container 20 of the delivery device 10 with the female luer tip of a vascular access device, after the distal end of said vascular access device has been placed in a blood vessel of a patient. The vascular access device includes a proximal end, a distal end, and a passageway therethrough, the proximal end having a female luer tip in fluid communication with the passageway. The user then depresses the primer element 30 to evacuate air within the chamber 23. The user applies force to the body of the deformable container to collapse the container 20 so that a solution located in the chamber 23 flows through the one-way valve into the vascular access device. After the expulsion of the desired amount of fluid from the chamber 23, the user disengages the male luer connector of the container 20 from the female luer of the vascular access device.

In one or more embodiments, the single use pre-filled delivery device 10 further includes a tip cap that is releasably connected to the male luer tip 27 of the deformable container 20 for sealing the passageway 28.

In one or more embodiments, the vascular access device is a syringe, extension set, intravenous set, stop cock, tubing, high pressure extension tubing, or needleless connector.

In one or more embodiments, the single use pre-filled delivery device 10 further includes a pre-selected amount of fluid in the chamber 23. The pre-selected amount of fluid in the chamber 23 may be from 0.5 ml to 10 ml. In one or more embodiments, the fluid may include a flush solution, drug or a medicament. The flush solution may be any solution intended for flushing or maintaining performance of VAD's. The flush solution may be selected from the group consisting of saline solution, water, heparin solution or a combination thereof. These solutions are known in the art and are readily available. The single-use pre-filled delivery device 10 may be pre-filled with flush solution, drug or medicament during or after the assembly of the syringe using sterile filling methods. Such prefilled assemblies may be supplied with a tip cap 45 that seals the passageway 28 of the deformable container 20 and male luer tip 27. The tip cap may be is formed of material selected from a group of thermoplastic materials and elastomeric materials such as natural and synthetic rubber, thermoplastic elastomers, combinations thereof, or other easily disposable and/or recyclable material. Once assembled, the syringe assembly may be used in flushing or administering a fluid to a VAD such as a catheter of an I.V. set.

The materials for the deformable container 20 will have to be chosen based not only on performance but on compatibility with the injectable liquid. In a preferred embodiment the single use pre-filled delivery device 10 is prefilled with injectable liquid. There may be a substantial amount of time between when the flush assembly is filled and when the contents of the flush assembly are delivered. Accordingly, materials chosen for single use pre-filled delivery device 10 may have to be stable under long term storage.

The deformable container 20, tip 27 and primer element 30 may be made of thermoplastic elastomers, natural rubber, synthetic rubber, thermoplastic materials, or other easily disposable and/or recyclable material and combinations thereof. Thermoplastic elastomers include, but are not limited to, polypropylene, polyethylene and the like. Materials should be chosen to be compatible with the solution, medicament and manufacturing process being used. It is envisioned that in one or more embodiments, the delivery device 10 of the present invention may be made of a single material to facilitate recycling of the device.

In one or more embodiments, the delivery device 10 further includes at least one protrusion on the primer element 30 for removing one or more air bubbles from the single use pre-filled delivery device 10 and controlling the delivery of fluid from the delivery device 10.

The single use pre-filled delivery device 10 of the present invention may be manufactured in accordance with a blow-fill-seal technique of a character well understood by those skilled in the art.

The concept of a blow-fill-seal process is that a container is formed, filled, and sealed as a unitary container in a continuous manner without human intervention in a sterile, enclosed area inside a machine. Blow-fill-seal manufacturing forms a closed container by extruding and forming a parison within a mold, filling the container and sealing the container in a single step. This manufacturing process enables the device to be produced in a single process. For example, pharmaceutical grade resin is extruded into a tube, which is then formed into a container. A mandrel is inserted into the newly formed container and filled. The container is then sealed, all inside a sterile, shrouded chamber. The product is then discharged to a non-sterile area for packaging and distribution. This blow-fill-seal technique comprises the continuous extrusion through an extruder head of a length of a parison in the form of a hollow tube between and through two co-acting first or main mold halves. The method includes the step of cutting off the parison below the extruder head and above the main mold halves to create an opening which allows a blowing and filling nozzle assembly to be moved downwardly into the opening in the parison for molding and thereafter filling a molded container. When the container portion of the container assembly is filled with the desired amount of liquid, the blowing and filling nozzle assembly is retracted from the opening in the parison. A separate pair of co-acting second or upper sealing mold halves are then moved together around the exposed length of parison to form and seal the container upper portion. The finished container assembly, completely formed, filled, and sealed as a unitary structure is then conveyed out of the molding apparatus.

A single use pre-filled delivery device 10 of the present invention reduces the risk associated with contamination due to manual filling a syringe with flush solution, drug or medicament from a vial.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A single use delivery device comprising:
   a manually deformable liquid container defining a non-corrugated inner chamber, the container having a distal end, a body, a proximal end, and an outlet on the distal end;
   a tip including a male luer connector projecting from the outlet on the distal end of the container, the tip in fluid communication with the inner chamber of the container; and
   a primer element positioned on the body of deformable liquid container, the primer element having a convex-shaped collapsible button disposed on the body of the deformable liquid container, the convex-shaped collapsible button having a volume that matches a volume of air bubbles contained in the deformable liquid container when the collapsible button is fully collapsed, the convex-shaped collapsible button assuming a concave surface upon manually depression by a user, said primer element being in fluid communication with the body of the deformable container; and
   the container, the tip and the primer element being collapsible to minimize dead space in the delivery device.

2. The single use delivery device of claim 1, wherein the primer element is assembled into the body of the container.

3. The single use delivery device of claim 1, wherein the primer element is molded into the body of the container.

4. The single use delivery device of claim 1, wherein the tip is releasably engageable to a vascular access device.

5. The single use delivery device of claim 1, wherein the vascular access device is a syringe, extension set, intravenous set, stop cock, tubing, high pressure extension tubing, or needleless connector.

6. The single use delivery device of claim 1, further comprising a pre-selected amount of fluid in the chamber.

7. The single use delivery device of claim 1, wherein the deformable container is made of thermoplastic elastomers.

* * * * *